United States Patent
Nakano et al.

(10) Patent No.: US 9,453,192 B2
(45) Date of Patent: Sep. 27, 2016

(54) HIGH-ACIDITY VINEGAR AND METHOD FOR PRODUCING THE SAME

(71) Applicants: Shigeru Nakano, Handa (JP); Takeshi Ohno, Handa (JP)

(72) Inventors: Shigeru Nakano, Handa (JP); Takeshi Ohno, Handa (JP)

(73) Assignee: MIZKAN HOLDINGS CO., LTD., Handa-Shi, Aichi (JP)

( * ) Notice: Subject to any disclaimer, the term of this patent is extended or adjusted under 35 U.S.C. 154(b) by 0 days.

(21) Appl. No.: 14/649,139

(22) PCT Filed: Dec. 3, 2012

(86) PCT No.: PCT/JP2012/081260
§ 371 (c)(1),
(2) Date: Jun. 2, 2015

(87) PCT Pub. No.: WO2014/087464
PCT Pub. Date: Jun. 12, 2014

(65) Prior Publication Data
US 2015/0315614 A1    Nov. 5, 2015

(51) Int. Cl.
C12P 7/54        (2006.01)
C07C 53/08       (2006.01)
C12J 1/04        (2006.01)
C12N 1/38        (2006.01)

(52) U.S. Cl.
CPC .................. *C12J 1/04* (2013.01); *C07C 53/08* (2013.01); *C12N 1/38* (2013.01); *C12P 7/54* (2013.01)

(58) Field of Classification Search
CPC ............ C12J 1/04; C07C 53/08; C12N 1/38; C12P 7/54
See application file for complete search history.

(56) References Cited

U.S. PATENT DOCUMENTS 4,384,936 A * 5/1983 Obana ................... C12Q 1/001
                                                    204/403.06
5,947,306 A * 9/1999 Chang ................... A47G 7/044
                                                    211/133.4

FOREIGN PATENT DOCUMENTS

| JP | 59137422    | * | 8/1984 |
|----|-------------|---|--------|
| JP | 62236479    | * | 10/1987 |
| JP | 63-84495 A  |   | 4/1988 |
| JP | 08-275769 A |   | 10/1996 |
| JP | 2006-230329 A |  | 9/2006 |

OTHER PUBLICATIONS

Heijthuijsen et al., "Selection of sulphur sources for the growth of Butyribacterium methylotrophicum and Acetobacterium woodii", Appl. Microbiol. Biotechnol., vol. 32, No. 2, pp. 186-192, 1989.
International Search Report issued in PCT/JP2012/081260 dated Jan. 15, 2013.
Shah et al., "Potassium Acetate by Fermentation with Clostridium thermoaceticum", Applied biochemistry and biotechnology, vol. 63-65, pp. 423-433, 1997.
Sim et al., "Optimization of acetic acid production from synthesis gas by chemolithotrophic bacterium-Clostridium aceticum using statisical approach", Bioresour. Technol., vol. 99, No. 8, pp. 2724-2735, 2008.

* cited by examiner

*Primary Examiner* — Shailendra Kumar
(74) *Attorney, Agent, or Firm* — Birch, Stewart, Kolasch & Birch, LLP

(57) ABSTRACT

The present invention relates to a method for producing a high-acidity vinegar with improved efficiency compared with conventional methods and a high-acidity vinegar obtained by such method. The method of the present invention is characterized in that acetic acid fermentation is conducted with a culture solution which contains a compound having a thiol group or an S-substituted derivative thereof or a compound having a disulfide bond as an additive wherein a total nitrogen content of the culture solution is 0.023 w/v % or less. According to the method of the present invention, a high-acidity vinegar, which has a total nitrogen content of 0.015 w/v % or less and an acidity of 10 to 25 w/v % and contains a compound having a thiol group or an S-substituted derivative thereof or a compound having a disulfide bond at a concentration of 17 μM or more in terms of sulfur atoms contained in the thiol group or disulfide bond can be obtained.

14 Claims, No Drawings

HIGH-ACIDITY VINEGAR AND METHOD FOR PRODUCING THE SAME

This application is a 371 of PCT/JP2012/081260, filed Dec. 3, 2012.

TECHNICAL FIELD

The present invention relates to a method for producing a high-acidity vinegar more efficiently than conventional methods and a high-acidity vinegar obtained by the method.

BACKGROUND ART

In acetic acid fermentation, it is known that proliferative capacity and fermentative capacity of acetic acid bacteria decrease as fermentation proceeds. The decrease in the fermentative capacity of an acetic acid bacterium along with the increase in acetic acid concentration in a culture solution is particularly significant in the production of high-acidity vinegars mainly used for industrial purposes. Therefore, improvement in culturing method and acetic acid bacterium used have been attempted in order to increase fermentation efficiency and the achievement level of acidity (acetic acid concentration) in a production of high-acidity vinegars.

For example, Patent Literature 1 discloses a method for producing an ultrahigh-acidity vinegar characterized in the gradually decrease of the fermentation temperature. In addition, Patent Literature 2 discloses a method for breeding an acetic acid bacterial strain with improved acetic acid tolerance.

CITATION LIST

Patent Literature

Patent Literature 1: JP Patent Publication (Kokai) No. 8-275769 A (1996)
Patent Literature 2: JP Patent Publication (Kokai) No. 2006-230329 A

SUMMARY OF THE INVENTION

Technical Problem

However, the effects obtained by the methods disclosed in Patent Literatures 1 and 2 are insufficient for practical use. There is a need to further improve the fermentative capacity of acetic acid bacteria for producing of high-acidity vinegars.

Solution to Problem

As a result of intensive studies on the above problem, the present inventors discovered that fermentation efficiency can be significantly improved by adding a specific compound to a culture solution for producing high-acidity vinegar. The present invention is summarized as follows.

(1) A method for producing a high-acidity vinegar wherein acetic acid fermentation is conducted with a culture solution which contains a compound having a thiol group or a S-substituted derivative thereof or a compound having a disulfide bond as an additive, wherein a total nitrogen content of the culture solution is 0.023 w/v % or less.

(2) The method according to (1), wherein the additive is selected from the group consisting of: amino acids having a thiol group and an S-substituted derivatives thereof; amino acids having a disulfide bond; and salts thereof.

(3) The method according to (1), wherein the additive is selected from the group consisting of cysteine, cystine, a peptide having a cysteine residue, and salts thereof.

(4) The method according to (1), wherein the additive is cystine or a salt thereof.

(5) The method according to any one of (1) to (4), wherein the culture solution contains the additive at a concentration of 20 μM or more in terms of sulfur atoms contained in the thiol group or disulfide bond.

(6) The method according to any one of (1) to (5), wherein the culture solution further contains glutamic acid or a salt thereof.

(7) The method according to any one of (1) to (6), wherein acetic acid fermentation is conducted until the acidity reaches 10 to 25 w/v %.

(8) A high-acidity vinegar produced by the method according to any one of (1) to (7).

(9) A high-acidity vinegar, wherein a total nitrogen content is 0.015 w/v % or less and an acidity is 10 to 25 w/v % and which contains a compound having a thiol group or an S-substituted derivative thereof or a compound having a disulfide bond at a concentration of 17 μM or more in terms of sulfur atoms contained in the thiol group or disulfide bond.

(10) The high-acidity vinegar according to (9), which contains a compound selected from the group consisting of cysteine, cystine, a peptide having a cysteine residue, and salts thereof.

(11) The high-acidity vinegar according to (9), which contains cystine.

(12) The high-acidity vinegar according to any one of (9) to (11), which further contains glutamic acid or a salt thereof.

Advantageous Effects of the Invention

According to the method of the present invention, acceleration in the acetic acid fermentation rate and shortening of the fermentation cycle time can be achieved merely by adding a step of adding a specific compound to a culture solution in a conventional method for producing a high-acidity vinegar. In addition, the high-acidity vinegar obtained by the method of the present invention has no difference in ingredients compared with a high-acidity vinegar produced by conventional methods other than the added compound. Therefore, according to the method of the present invention, it is possible to improve production efficiency of a high-acidity vinegar while maintaining product quality.

DESCRIPTION OF EMBODIMENTS

The present invention relates to a method for producing a high-acidity vinegar having acidity of 10% to 25%, particularly 15% to 25% by brewing, i.e., acetic acid fermentation. In general, the acidity of vinegar means the concentration of acetic acid (w/v %) in the vinegar. The acidity referred to herein means the acetic acid concentration determined by conducting neutralization titration of the sample (vinegar) with phenolphthalein as an indicator and 1N sodium hydroxide aqueous solution in the manner known to persons skilled in the art.

Any acetic acid bacterium can be used for acetic acid fermentation as long as it is tolerable to fermentation in which acidity is increased to a high level. Among acetic acid bacteria, bacteria of the genus *Acetobacter* or the genus

*Gluconacetobacter* are preferred. Among the bacteria of the genus *Acetobacter*, *Acetobacter aceti*, in particular *Acetobacter aceti* No. 1023 (FERM BP-2287), *Acetobacter pasteurianus* NBRC3283, and *Acetobacter altoacetigenes* MH-24 (FERM BP-491) can be used, for example. Among the bacteria of the genus *Gluconacetobacter*, *Gluconacetobacter europaeus* DSM6160, *Gluconacetobacter entanii*, and *Gluconacetobacter xylinus* NBRC3288 can be used, for example.

It is desirable to use the minimum types and amounts of raw materials for preparing a culture solution for acetic acid fermentation from the viewpoints of that high-acidity vinegars are desired to have mild flavors and tastes and that there is a need of production cost suppression. However, in order to support the growth of acetic acid bacteria, it is preferable to add nutrient sources for acetic acid bacteria into the culture solution. Examples of such nutrient sources include microorganism extracts (e.g., yeast extract), sugars (e.g., glucose, fructose, sucrose, and dextrose), and peptone. Commercially available nutrient sources (e.g., Acetozym (FRINGS) and Nutri-Go 1500 (Nutrients)) may be used.

The composition of the culture solution may be composed of 4 to 10 w/v % of acetic acid, 1 to 4 v/v % of ethanol, and 0.005 to 1 w/v % of nutrient sources. Acetic acid may be fermented vinegar or synthetic acetic acid, however, fermented vinegar is preferably used. Alcohol for brewing (e.g., 99.5 v/v % alcohol or 95 v/v % alcohol) can be used as ethanol.

The method for producing a high-acidity vinegar of the present invention is characterized in that a compound having a thiol group or an S-substituted derivative thereof or a compound having a disulfide bond is added as an additive to a culture solution. The acetic acid fermentation rate can be accelerated with the addition of a compound having a thiol group (—SH) or an S-substituted derivative thereof or a compound having a disulfide bond (—S—S—).

Examples of a compound having a thiol group are described below.

Amino Acids Having a Thiol Group and Salts Thereof:
For example, cysteine or homocysteine and salts thereof are included. In addition, peptides having a residue of such amino acid (in particular, oligopeptides composed of 2 to 10 amino acids bound to each other, especially dipeptides, tripeptides, and tetrapeptides, e.g., glutathione) are also encompassed in amino acids having a thiol group described herein. In addition, examples of salts of amino acids include salts with alkali metals (e.g., potassium and sodium) and alkaline earth metals (e.g., calcium and magnesium). Amino acids may be in the L-form or D-form; however, amino acids in the L-form are more preferable.

Other Compounds Having a Thiol Group:
Examples of a compound having a thiol group include benzenemethanethiol, benzenethiol, bis(1-mercaptopropyl) sulfide, 1,4-butanedithiol, 2,3-butanedithiol, 2-butanethiol, butanethiol, cyclohexanethiol, cyclopentanethiol, 2,3-dimercaptopropanol, 2,6-dimethylbenzenethiol, 3,3-dimethylbutanethiol, 2,5-dimethyl-3-furanthiol, 1,1-dimethylheptanethiol, 1,1-dimethylheptanethiol, dimethylthiophenol, dodecanethiol, 1,2-ethanedithiol, ethanedithiol, ethanethiol, 4-ethoxy-2-methyl-2-butanethiol, 2-(ethylthio)phenol, 2-furanmethanethiol, 2-heptanethiol, heptanethiol, hexadecanethiol, 1,6-hexanedithiol, hexanethiol, 3-hydroxy-2-butanethiol, 2-hydroxyethanethiol, 3-hydroxy-2-methylbutanethiol, isobutylthiol, mercaptoacetaldehyde diethylacetal, 2-mercaptobenzothiazole, 3-mercapto-1-hexanol, 3-mercapto-2-methylbutanol, 3-mercapto-3-methylbutanol, 3-mercapto-2-methylpentanol, 4-mercapto-4-methyl-2-pentanol, 3-[(2-mercapto-1-methylpropyl)thio]-2-butanol, (2 or 3 or 10)-mercaptopinane, methanedithiol, methanethiol, 2-methoxybenzenethiol, 4-methoxy-2-methyl-2-butanethiol, 2-methylbenzenethiol, 2-methylbutanethiol, 3-methyl-2-butanethiol, 3-methyl-2-butenethiol, 2-methyl-4,5-dihydro-3-furanthiol, 5-methyl-2-furanmethanethiol, 2-methyl-3-furanthiol, 2-methyl-3-(2-methyl-2(4),5-dihydro-3-furanylthio)-3-tetrahydrofuranthiol, 3-{[2-methyl-(2 or 4),5-dihydro-3-furyl]thio}-2-methyltetrahydrofuran-3-thiol, (4-methylphenyl)methanethiol, 2-methyl-2-propanethiol, 2-methyl-3-tetrahydrofuranthiol, 2-naphthalenethiol, 1,9-nonanedithiol, 1,8-octanedithiol, octanethiol, 2,4,4,6,6-pentamethyl-2-heptanethiol, 2-pentanethiol, 3-pentanethiol, 1-phenylethanethiol, 2-phenylethanethiol, 1-p-menthene-8-thiol, prenyl mercaptan, 1,1-propanedithiol, 1,2-propanedithiol, 1,3-propanedithiol, 2-propanethiol, 2-propenethiol, 2-pyrazinylethanethiol, 2-pyridinylmethanethiol, 2-thiazoline-2-thiol, 2-thiazoline-2-thiol, 1-(2-thienyl)ethanethiol, 2-thienylmethanethiol, thiogeraniol, thiolinalool, 2-thiophenethiol, and thioterpineol.

S-substituted derivatives of the above compounds having a thiol group can also be used as additives. Examples of substituents on S of S-substituted derivative include $C_{1-6}$ alkyl (e.g., methyl, ethyl, n-propyl, isopropyl, n-butyl, sec-butyl, or t-butyl), $C_{1-6}$ alkoxy (e.g., methoxy, ethoxy, n-propoxy, isopropoxy, n-butoxy, sec-butoxy, or t-butoxy), $C_{1-6}$ alkynyl (e.g., allyl, propenyl, or butenyl), phenyl, and benzyl. Specific examples of an S-substituted derivative of a compound having a thiol group include S-methylcysteine, S-allylcysteine, S-1-propenylcysteine, and methionine. Regarding the above S-substituted derivatives, it is more preferable that substituents on S be relatively easily eliminated and converted into a thiol group.

Examples of a compound having a disulfide bond include a dimer of the compounds having a thiol group as above obtained via a disulfide bond formation, in particular amino acids having a disulfide bond which corresponds to a dimer of an amino acid having a thiol group, and salts thereof. Specific examples thereof include cystine, which is a dimer of cysteine, and salts thereof. A compound having a disulfide bond can be cleaved by reduction of the disulfide bond and converted into two molecules of a compound having a thiol group.

Preferably, an additive used in the present invention is an amino acid having a thiol group or an S-substituted derivative thereof, or an amino acid having a disulfide bond, or salts thereof. A particularly preferable additive is a compound selected from the group consisting of cysteine, cystine, peptides having a cysteine residue (in particular, glutathione), and salts thereof. The form of the additive is not particularly limited. The additive may be added as a pure form. Alternatively, the additive may be added in a form of natural product such as yeast extract or extract of other bacteria, plants or animals containing the above exemplified compound (e.g., glutathione).

When the additive is added in a manner such that a culture solution contains the additive at a concentration of 20 μM or more, more preferably 36 μM or more, particularly 36 to 360 μM, and especially 36 to 180 μM in terms of sulfur atoms contained in the thiol group or disulfide bond, sufficient effect of accelerating the acetic acid fermentation rate can be achieved. In a compound having a thiol group or an S-substituted derivative thereof or a compound having a disulfide bond used as an additive, the concentration "in terms of sulfur atoms contained in the thiol group or disulfide bond" means the concentration based on the number of sulfur atoms contained in a thiol group or a disulfide bond or, when the compound is S-substituted derivative of a compound having a thiol group, the number of sulfur atoms derived from the thiol group. Therefore, in the case of cysteine or glutathione which contains only one thiol group including one sulfur atom, the concentration is equal to the molar concentration of the molecule. In the case of cystine which contains one disulfide bond including two sulfur atoms, the concentration corresponds to twice the molar concentration of the molecule. For example, the concentration of 1M cystine in terms of sulfur atoms is 2M.

In addition to the above additive, namely a compound having a thiol group or an S-substituted derivative thereof or a compound having a disulfide bond, addition of glutamic acid or a salt thereof to the culture solution may further accelerate the acetic acid fermentation rate. Glutamic acid may be in the L-form or D-form, however, L-form is more preferable. Examples of salts of glutamic acid include salts with an alkali metal (e.g., potassium or sodium) or an alkaline-earth metal (e.g., calcium or magnesium). The acceleration effect on the acetic acid fermentation rate achieved with the addition of a compound having a thiol group or an S-substituted derivative thereof or a compound having a disulfide bond can be further enhanced by adding glutamic acid or a salt thereof in a manner such that the concentration thereof in the culture solution reaches 20 μM or more, preferably 36 μM or more, more preferably 72 μM or more, particularly 72 to 520 μM, and especially 72 to 360 μM.

As already stated, it is desirable to use the minimum types and amounts of raw materials for preparing a culture solution for production of high-acidity vinegars. Therefore, the content of nutritional components such as amino acids in the culture solution is considerably low as compared to the one used in a production of low-acidity vinegars. Though details of the mechanism have not been elucidated, it has been confirmed that the acceleration effect on acetic acid fermentation rate with the addition of the additive to a culture solution as stated above is particularly significant upon production of high-acidity vinegars in which the culture solution contains fewer nutritional components such as amino acids. The effect achieved by the method of the present invention become significant when the total nitrogen content in the culture solution after adding of the additive (in certain cases, glutamic acid or a salt thereof may be included) is 0.023 w/v % or less, particularly 0.015 w/v % or less, and especially 0.01 w/v % or less. The term "total nitrogen content" used herein means a value obtained by determining the total content of inorganic nitrogen and organic nitrogen by chemiluminescence assay.

It has been confirmed that approximately 90% of the used amount of the additive added to the culture solution remains in a high-acidity vinegar obtained as a product. Therefore, it is considered that the additive is not merely a nutrient source used by an acetic acid bacteria but functions like a catalyst to improve the acetic acid production capacity of the acetic acid bacterium. Since the additive added to the culture solution remains in a product, it is preferable for the additive to be acceptable as a food additive.

The method for producing a high-acidity vinegar of the present invention is similar to conventional methods except that the aforementioned additive is added to the culture solution. Any conventionally known fermentation technique such as submerged fermentation involving aeration stirring, batch fermentation, semi-continuous fermentation, or two-stage fermentation can be used. In addition, regarding an aeration technique, aeration can be conducted by supplying a gas containing oxygen such as air or oxygen gas via an aeration pipe as in conventional techniques. For example, when submerged fermentation involving aeration and stirring is adopted, air is supplied to a lower part of fermentation liquid at an aeration volume of 0.02 to 1 vvm (aeration volume/fermentation liquid volume/minute) and dispersed by a stirrer such that the dissolved oxygen level in the fermentation liquid is maintained at approximately 0.2 to 8 ppm. Since ethanol is consumed as acetic acid fermentation proceeds, fermentation is conducted with supplying ethanol so as to maintain the ethanol concentration in the culture solution at 1.5 to 3 v/v %, for example.

The fermentation temperature is preferably 15° C. to 40° C. and particularly preferably 25° C. to 35° C. To set the fermentation temperature of 30° C. or less after the acidity exceeds 10% so as to reduce the impairment on acetic acid bacteria due to acetic acid, a vinegar with a higher acidity can be produced. In most cases, it takes approximately 20 hours to 30 days per instance of production though the fermentation time varies depending on the nature of acetic acid bacteria to be used, the conditions of seed bacteria (e.g., freeze-dried, frozen, slant, liquid culture), medium composition, the manner of supplying the medium, aeration stirring conditions, and the like.

The high-acidity vinegar of the present invention obtained by the method described above is characterized in that the total nitrogen content is 0.015 w/v % or less, particularly 0.01 w/v % or less, and especially 0.007 w/v % or less, the acidity is 10 to 25 w/v %, and specifically 15 to 25 w/v %, and it contains a compound having a thiol group or an S-substituted derivative thereof or a compound having a disulfide bond. In addition, in the case where glutamic acid or a salt thereof is added to the culture solution, the obtained high-acidity vinegar also contains glutamic acid or a salt thereof. The concentration of an additive remaining in the high-acidity vinegar of the present invention is approximately 85% to 95% of the concentration of the additive in the culture solution. Therefore, the concentration of a compound having a thiol group or an S-substituted derivative thereof or a compound having a disulfide bond in the high-acidity vinegar of the present invention is 17 μM or more, more preferably 32 μM or more, particularly 32 to 320 μM, and especially 32 to 162 μM in terms of sulfur atoms contained in the thiol group or disulfide bond. In addition, the concentration of glutamic acid or a salt thereof is 17 μM or more, more preferably 32 μM or more, further preferably 64 μM or more, particularly 64 to 640 μM, and especially 64 to 324 μM. Except for the above additives, the other components of the high-acidity vinegar of the present invention are similar to those of conventional high-acidity vinegar produced without the additive.

EXAMPLES

The present invention is hereinafter described in detail with reference to the following examples, although the scope of the present invention is not limited thereto.

Example 1

A culture solution (2.5 L) containing acetic acid (8 w/v %), ethanol (2 v/v %), Acetozym DS+2 (product of FRINGS; 0.15 w/v %), and a variety of additives at given concentrations was introduced into a 5 L-volume jar fermenter. The total nitrogen content of the culture solution was 0.006 w/v %. Cryopreserved *Acetobacter altoacetigenes* MH-24 (FERM BP-491) was inoculated into the culture solution to start acetic acid fermentation. Submerged fermentation involving aeration stirring was adopted for the fermentation. Fermentation was conducted under the conditions of a temperature at 30° C., a rotative speed of 600 rpm, and an aeration volume of 0.15 vvm.

After the start of fermentation, 95% ethanol was fed to the fermentation liquid until the acidity (acetic acid concentration: w/v %) of the fermentation liquid exceeded 15% so as to maintain the ethanol concentration in the fermentation liquid at 1.5 to 3 v/v %. At the time point at which the acidity exceeded 15% (approximately 15.5%) and the ethanol concentration reached about 0.5 v/v %, the fermentation liquid was pulled out such that approximately half of the total fermentation liquid volume is remained.

After the portion of the fermentation liquid was pulled out, the above components were added again without discontinuation of aeration and stirring of the remaining fermentation liquid such that the volume of the fermentation liquid was adjusted to 2.5 L and the composition of the fermentation liquid became equivalent to the composition of the original culture solution. Then, fermentation was continued in the above manner. Thereafter the cycle, in which fermentation was conducted until the acidity exceeded 15% (approximately 15.5%), approximately half of the total volume of the fermentation liquid was pulled out and the above components were added again to restart fermentation with decreased acidity, is repeated to conduct semi-continuous fermentation. Seven times repeats of the cycle from the start of fermentation to re-introduction of the components was regarded as one examination. Six examinations were conducted with each different condition of additives. Table 1 summarizes the average time duration required for one cycle, i.e., from the restart of fermentation to the time point at which the acidity exceeded 15%, (the average time of 2nd to 7th cycles), final acidity (acidity when a portion of the fermentation liquid was pulled out), and productivity (the rate of increase in acidity per hour) with the types and amounts of additives.

TABLE 1

| | Additive (concentration) | Fermentation time (h) | Final acidity (%) | Productivity (%/h) |
|---|---|---|---|---|
| Exam 1 (Control) | None | 51.0 | 15.1 | 0.139 |
| Exam 2 | L-cystine 18 μM | 48.9 | 15.4 | 0.151 |
| Exam 3 | L-cystine 45 μM | 41.7 | 15.3 | 0.175 |
| Exam 4 | L-cystine 90 μM | 37.5 | 15.3 | 0.195 |
| Exam 5 | L-cystine 18 μM + L-glutamic acid 162 μM | 35.8 | 15.3 | 0.205 |

In Exams 2 to 5 in which L-cystine or a combination of L-cystine and L-glutamic acid was used as an additive, improvement of productivity was confirmed as compared with Exam 1 in which no additive was used. In particular, when L-cystine was used alone, the effect of improving productivity was confirmed even at a low concentration of 18 μM (Exam 2). It was also confirmed that the addition of L-glutamic acid in addition to L-cystine resulted in further enhancement of the effect of improving productivity (Exam 5). In addition, the average total nitrogen content for the vinegars obtained in Exams 2 to 5 was 67% of the total nitrogen content of the culture solution.

Example 2

Fermentation was conducted as in Example 1 except that a culture solution containing Nutri-Go 1500 (product of Nutrients; 0.06 w/v %) and dextrose (0.12 w/v %) instead of Acetozym DS+2 was used and the number of cycle repetitions was 4. The results are shown in Table 2. It was confirmed that productivity was significantly improved also when glutathione was used as an additive.

TABLE 2

| | Additive (concentration) | Fermentation time (h) | Final acidity (%) | Productivity (%/h) |
|---|---|---|---|---|
| Exam 1 (Control) | None | 63.5 | 15.4 | 0.117 |
| Exam 2 | Glutathione 220 μM | 51.3 | 15.4 | 0.144 |

All publications, patents, and patent applications cited herein are incorporated herein by reference in their entirety.

The invention claimed is:

1. A method for producing a high-acidity vinegar comprising:
   preparing a culture solution comprising at least one additive selected from the group consisting of:
   a compound having a thiol group or an S-substituted derivative thereof, and
   a compound having a disulfide bond; and
   conducting acetic acid fermentation with the culture solution using bacteria of the genus *Acetobacter* or the genus *Gluconacetobacter*, wherein a total nitrogen content of the culture solution is 0.023 w/v % or less.

2. The method according to claim 1, wherein the additive is selected from the group consisting of: amino acids having a thiol group and S-substituted derivatives thereof amino acids having a disulfide bond; and salts thereof.

3. The method according to claim 1, wherein the additive is selected from the group consisting of cysteine, cystine, peptides having a cysteine residue, and salts thereof.

4. The method according to claim 1, wherein the additive is cystine or a salt thereof.

5. The method according to claim 1, wherein the culture solution contains the at least one additive at a concentration of 20 μM or more in terms of sulfur atoms contained in the thiol group or disulfide bond.

6. The method according to claim 2, wherein the culture solution contains the at least one additive at a concentration of 20 μM or more in terms of sulfur atoms contained in the thiol group or disulfide bond.

7. The method according to claim 3, wherein the culture solution contains the at least one additive at a concentration of 20 μM or more in terms of sulfur atoms contained in the thiol group or disulfide bond.

8. The method according to claim 4, wherein the culture solution contains the at least one additive at a concentration of 20 μM or more in terms of sulfur atoms contained in the thiol group or disulfide bond.

9. The method according to claim 1, wherein the culture solution further comprises glutamic acid or a salt thereof.

10. The method according to claim 2, wherein the culture solution further comprises glutamic acid or a salt thereof.

11. The method according to claim 3, wherein the culture solution further comprises glutamic acid or a salt thereof.

12. The method according to claim 4, wherein the culture solution further comprises glutamic acid or a salt thereof.

13. The method according to claim 5, wherein the culture solution further comprises glutamic acid or a salt thereof.

14. The method according to claim 1, wherein acetic acid fermentation is conducted with said culture solution until acidity of the culture solution reaches 10 to 25 w/v %.

\* \* \* \* \*